US009630231B2

(12) United States Patent
Kelsch et al.

(10) Patent No.: US 9,630,231 B2
(45) Date of Patent: Apr. 25, 2017

(54) SUPERPLASTIC FORMING FOR TITANIUM IMPLANT ENCLOSURES

(75) Inventors: Daniel N. Kelsch, Fairview Park, OH (US); Alexander K. Smith, Chesterland, OH (US); Francis J. Toal, Plymouth, MN (US)

(73) Assignee: NUVECTRA CORPORATION, Plano, TX (US)

( * ) Notice: Subject to any disclaimer, the term of this patent is extended or adjusted under 35 U.S.C. 154(b) by 1419 days.

(21) Appl. No.: 13/359,652

(22) Filed: Jan. 27, 2012

(65) Prior Publication Data
US 2013/0197610 A1 Aug. 1, 2013

(51) Int. Cl.
B21D 26/055 (2011.01)
B21D 22/02 (2006.01)
B21D 26/021 (2011.01)
A61N 1/375 (2006.01)

(52) U.S. Cl.
CPC ......... B21D 26/055 (2013.01); B21D 22/022 (2013.01); B21D 26/021 (2013.01); *A61N 1/375* (2013.01); *Y10T 29/301* (2015.01); *Y10T 29/49002* (2015.01)

(58) Field of Classification Search
CPC .. B21D 26/055; B21D 26/021; B21D 22/022; A61N 1/375; Y10T 29/301; Y10T 29/49002
See application file for complete search history.

(56) References Cited

U.S. PATENT DOCUMENTS

| 3,920,175 | A | 11/1975 | Hamilton et al. |
| 4,250,727 | A | 2/1981 | Baril et al. |
| 4,294,419 | A | 10/1981 | Fouse et al. |
| 4,350,155 | A | 9/1982 | Thompson |
| 4,951,491 | A | 8/1990 | Lorenz |
| 5,336,246 | A | 8/1994 | Dantanarayana |
| 5,823,034 | A | 10/1998 | Nelepovitz |
| 5,843,142 | A | 12/1998 | Sultan |
| 5,991,665 | A | 11/1999 | Wang et al. |
| 6,029,269 | A * | 2/2000 | El-Soudani ............. A42C 2/00 2/2.5 |
| 6,033,506 | A | 3/2000 | Klett |
| 6,038,475 | A | 3/2000 | Sikorski et al. |
| 6,116,070 | A | 9/2000 | Oshida et al. |
| 6,131,651 | A | 10/2000 | Richey, III |
| 6,287,118 | B1 | 9/2001 | Naganuma et al. |
| 6,313,031 | B1 | 11/2001 | Schuele et al. |
| 6,432,142 | B1 | 8/2002 | Kamiya et al. |
| 6,517,534 | B1 | 2/2003 | McGovern et al. |
| 6,550,124 | B2 | 4/2003 | Krajewski et al. |

(Continued)

FOREIGN PATENT DOCUMENTS

WO 0102632 1/2001

*Primary Examiner* — Peter DungBa Vo
*Assistant Examiner* — Jeffrey T Carley
(74) *Attorney, Agent, or Firm* — Pearne & Gordon LLP

(57) ABSTRACT

A titanium alloy metal sheet is provided and heated to a superplastic forming temperature. A die has a plurality of housing forming areas each corresponding to one of the medical device housing portions. The heated titanium alloy metal sheet is forced onto the die and over each one of the plurality of housing forming areas, thereby superplastically forming a workpiece comprising a plurality of integrally formed implantable medical device housing portions.

14 Claims, 10 Drawing Sheets

(56) References Cited

U.S. PATENT DOCUMENTS

| | | |
|---|---|---|
| 6,655,575 B2 | 12/2003 | Mishra |
| 6,660,116 B2 | 12/2003 | Wolf et al. |
| 6,694,790 B2 | 2/2004 | Ryntz et al. |
| 6,765,779 B2 | 7/2004 | Stevenson et al. |
| 6,776,214 B2 | 8/2004 | Ray et al. |
| 6,888,715 B2 | 5/2005 | Stevenson et al. |
| 7,225,032 B2 | 5/2007 | Schmeling et al. |
| 7,232,625 B2 | 6/2007 | Leysieffer et al. |
| 7,261,782 B2 | 8/2007 | Hwang et al. |
| 7,351,240 B2 | 4/2008 | Hassler, Jr. et al. |
| 7,494,488 B2 | 2/2009 | Weber |
| 7,499,260 B2 | 3/2009 | Schott et al. |
| 7,533,794 B2 | 5/2009 | Comley et al. |
| 7,713,651 B2 | 5/2010 | Leysieffer et al. |
| 7,848,817 B2 | 12/2010 | Janzig et al. |
| 7,901,509 B2 | 3/2011 | Mariner et al. |
| 8,066,712 B2 | 11/2011 | Truckai et al. |
| 8,180,453 B2 | 5/2012 | Greenberg et al. |
| 8,260,435 B2 | 9/2012 | Johnson et al. |
| 8,267,983 B2 | 9/2012 | Rogers et al. |
| 8,339,769 B2 | 12/2012 | Schott et al. |
| 8,380,302 B2 | 2/2013 | Schmalhurst et al. |
| 8,430,887 B2 | 4/2013 | Truckai et al. |
| 8,437,865 B2 | 5/2013 | Dabney et al. |
| 2003/0047253 A1 | 3/2003 | Robinson et al. |
| 2003/0097178 A1 | 5/2003 | Roberson et al. |
| 2003/0124029 A1* | 7/2003 | Webb .................. G01N 35/028 435/287.2 |
| 2008/0103556 A1* | 5/2008 | Li .......................... A61N 1/375 607/61 |
| 2008/0168775 A1 | 7/2008 | Windheim et al. |
| 2008/0264464 A1 | 10/2008 | Lee et al. |
| 2008/0294207 A1 | 11/2008 | Kast et al. |
| 2010/0256709 A1 | 10/2010 | Kallmyer |
| 2011/0009773 A1 | 1/2011 | Hower et al. |
| 2011/0295347 A1 | 12/2011 | Wells et al. |
| 2012/0299175 A1 | 11/2012 | Tran |
| 2012/0310313 A1 | 12/2012 | Rogers et al. |
| 2013/0078149 A1 | 3/2013 | Holmes et al. |

\* cited by examiner

SUPERPLASTIC FORMING FOR TITANIUM IMPLANT ENCLOSURES

BACKGROUND OF THE INVENTION

Field of the Invention

This disclosure is directed to medical implant devices and the manufacture thereof.

Description of Related Art

Medical devices capable of being implanted in a body are known as medical implant devices, implantable medical devices, medical implants, etc. Cases or housings for such devices can be constructed from titanium and titanium alloys. Pure titanium, for example Grade 1 titanium, is generally easier to cold form than titanium alloys, and has a lower electrical resistivity than titanium alloys. At room temperature, Grade 1 titanium has an elongation of about 30%, whereas a titanium alloy might only have 10% to 15% elongation, making the titanium alloy more difficult to cold form. With titanium alloys, excessive spring-back and cracking can be exhibited in areas of large deformation when cold forming these materials into shapes suitable for compact implantable medical devices. This can lead to design compromises when designing a titanium alloy housing for an implantable medical device. Such design compromises can include larger radii for curves on the housing, more generous tolerances, etc. Hot stamping the titanium alloy might be employed to slightly increase the elongation percent, but the design freedom for the housing will still be limited. Moreover, both hot and cold stamping typically require a post vacuum annealing procedure in order to reduce residual stress and remove surface formation of brittle alpha case, caused by processing in ambient air, that can lead to microcracking and reduced fatigue life.

SUMMARY

This disclosure is directed to medical implant devices and the manufacture thereof. More particularly, this disclosure is directed to methods of manufacturing titanium alloy implantable medical device housing portions (e.g., front and rear housing portions that can be assembled), methods of manufacturing implantable medical devices, and methods of providing a therapy to a patient using implantable medical devices.

In accordance with one example method, a titanium alloy metal sheet is provided and heated to a superplastic forming temperature. A die is also provided. The die has a plurality of housing forming areas each corresponding to one of the housing portions. The heated titanium alloy metal sheet is forced onto the die and over each one of the plurality of housing forming areas, thereby superplastically forming a workpiece comprising a plurality of integrally formed implantable medical device housing portions.

In accordance with another example method, a titanium alloy metal sheet is provided and heated to a superplastic forming temperature. A die is also provided. The die has a plurality of cavities each corresponding to one of the housing portions. The heated titanium alloy metal sheet is forced into each one of the plurality of cavities simultaneously, thereby superplastically forming a workpiece comprising a plurality of joined and integrally formed implantable medical device housing portions formed simultaneously.

In accordance with another example method, a titanium alloy metal sheet is provided and heated to a superplastic forming temperature. A die is also provided. The die has a plurality of housing forming areas each corresponding to one of the housing portions. The heated titanium alloy metal sheet is forced onto the die and over each one of the plurality of housing forming areas simultaneously, thereby superplastically forming a workpiece comprising a plurality of joined and simultaneously integrally formed implantable medical device housing portions. Each housing portion includes a first edge portion located between a first set of rounded corners, and a second edge portion located between a second set of rounded corners. A radius for the second set of rounded corners is at least three times larger than a radius for the first set of rounded corners. The first edge portion extends along a substantially straight line between the first set of rounded corners, and the second edge portion extends along a curve between the second set of rounded corners. Each housing portion includes third and fourth edge portions extending between the first set of rounded corners and the second set of rounded corners, and the third and fourth edge portions are curved.

In accordance with another example method, a titanium alloy metal sheet is provided. The titanium alloy metal sheet is heated to a superplastic forming temperature. A die is also provided. The die has a plurality of housing forming areas each corresponding to one of the housing portions. The heated titanium alloy metal sheet is forced onto the die and over each one of the plurality of housing forming areas simultaneously, thereby superplastically forming a workpiece comprising a plurality of joined and simultaneously integrally formed implantable medical device housing portions. The plurality of integrally formed implantable medical device housing portions are separated into separate housing portions. A plurality of feed through holes are cut into at least one of the housing portions, and pulse generation circuitry is installed therein, including aligning feed through pins with the plurality of feed through holes. At least one of the housing portions is welded to another housing portion from said or another workpiece.

In accordance with another example method, a titanium alloy metal sheet is provided. The titanium alloy metal sheet is heated to a superplastic forming temperature. A die is also provided. The die has a plurality of housing forming areas each corresponding to one of the housing portions. The heated titanium alloy metal sheet is forced onto the die and over each one of the plurality of housing forming areas simultaneously, thereby superplastically forming a workpiece comprising a plurality of joined and simultaneously integrally formed implantable medical device housing portions. The plurality of integrally formed implantable medical device housing portions are separated into separate housing portions. A plurality of feed through holes are cut into at least one of the housing portions, and pulse generation circuitry is installed therein, including aligning feed through pins with the plurality of feed through holes. At least one of the housing portions is welded to another housing portion from said or another workpiece. A header is attached to the at least one of the housing portions thereby forming an implantable medical device. The header encloses at least one connector comprising contact blocks that are respectively electrically connected to the feed through pins. The implantable medical device and an electrode are implanted into a body of a patient. Electrical pulses are generated by the implantable medical device. The pulses are transmitted to a portion of the body by the electrode.

DETAILED DESCRIPTION

Figure 1:
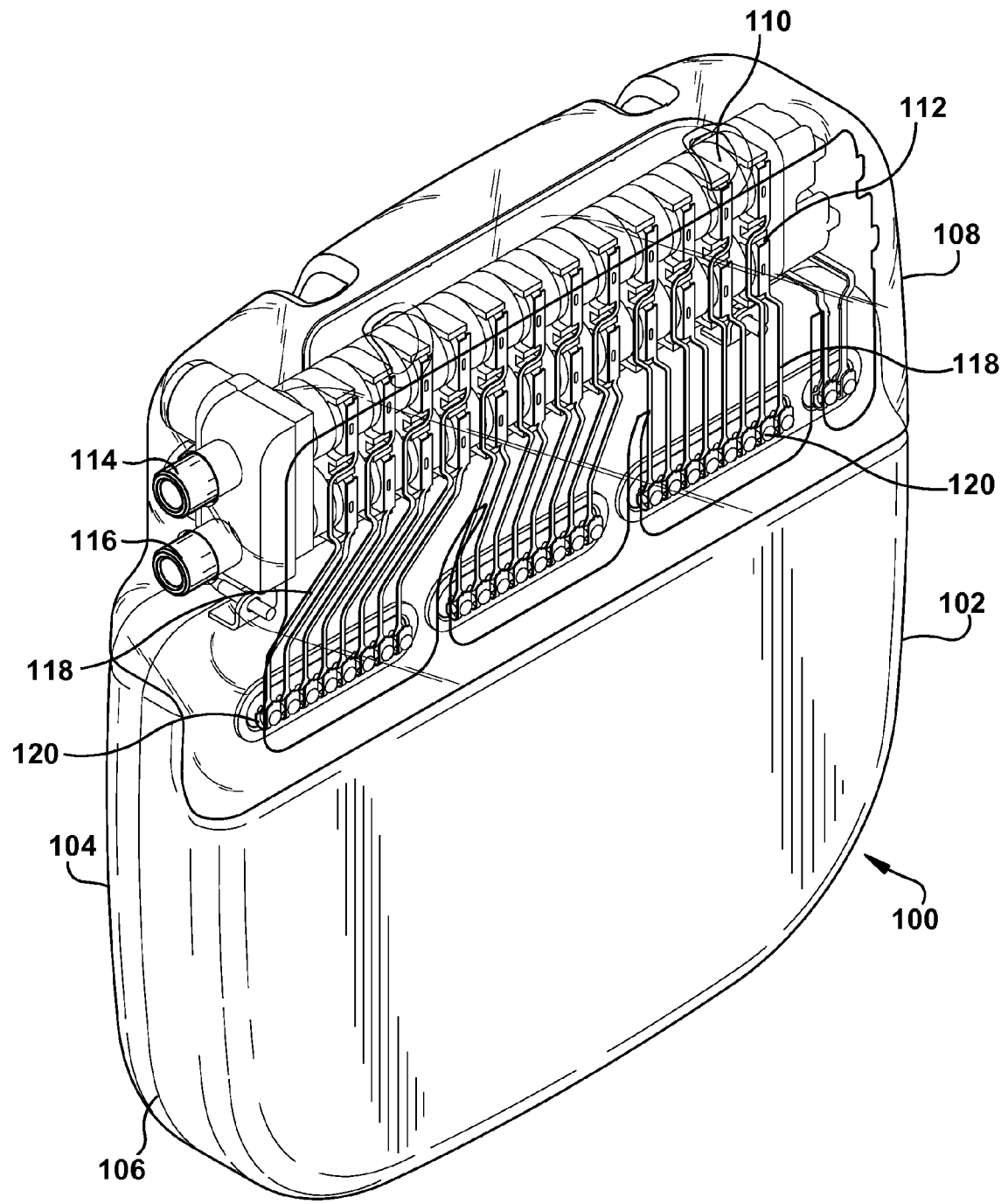
FIG. 1 is a perspective view of an example implantable medical device.

Example implantable medical devices include implantable pulse generators (IPG) (e.g., spinal cord stimulators, neurostimulators, etc.), implantable cardiac pacemakers, implantable drug infusion pumps, implantable cardiac defibrillators, and the like. Some implantable medical devices are rechargeable. Rechargeable implantable medical devices can be recharged inductively, by a charger located outside of the body inducing a charging current in a coil located within the implantable medical device.

Forming a housing for the rechargeable implantable medical device out of a titanium alloy (e.g., Ti-6Al-4V ELI (extra-low interstitial) alloy or Grade 23, Ti-3Al-2.5V alloy or Grade 9, etc.), rather than pure titanium, can provide advantages due to the higher electrical resistivity of titanium alloys. The higher electrical resistivity of titanium alloys reduces eddy currents that form in the housing during charging. Eddy currents are generally undesirable because they can heat the housing to unacceptably high temperatures and they reduce charging efficiency. Eddy currents can be controlled by reducing the power transmitted by the charger to the implantable medical device. However, reducing the power increases charging time. Thus, using titanium alloy rather than pure titanium for housings of rechargeable implantable medical devices provides the advantages of decreased surface heating and more efficient and quicker charging of the device.

However, titanium alloy housings formed using conventional cold and hot stamping processes can require design compromises, as discussed above. Further, both hot and cold stamping typically require a post vacuum annealing procedure. An alternative to conventional hot and cold stamping processes that can reduce design constraints and eliminate the need for a subsequent annealing procedure is to superplastic form the housings. Superplastic forming the housing can be more expensive than conventional cold and hot stamping processes. However, such increased cost can be offset by producing housing parts for multiple implant devices simultaneously, from a single sheet of titanium alloy.

Superplastic forming involves heating a metal (e.g., a titanium alloy sheet) having a very fine micrograin structure to a temperature at which the flow stress of the material is low. For a titanium alloy, such a temperature might be approximately 1650° F. or 900° C. At such temperatures, the alloy can be formed with elongations exceeding 100%, thereby reducing the design constraints associated with stamped parts. To form the housing parts, the heated alloy sheet is forced onto a die having a plurality of forming areas (e.g., cavities or projections) that correspond to the housing parts to be formed. The die and/or a press component of the superplastic forming device can be used to heat the alloy sheet before and while it is forced onto the die. The superplastic forming device can employ an inert gas, such as argon gas, to force the heated alloy sheet onto the die. The application of an inert gas can reduce or eliminate the formation of undesirable alpha case on the surface of the parts, and the high temperatures employed in superplastic forming leave the resulting parts stress free, so no additional annealing is required. If desired, diffusion bonding of additional parts onto the housing parts can occur at the time of superplastic forming.

Turning to the figures, FIG. 1 provides a perspective view of an example implantable medical device 100. The implantable medical device includes a front housing portion 102 and a rear housing portion 104 each formed from a titanium alloy metal sheet (e.g., by superplastic forming). The front and rear housing portions are attached to each other in a sealed manner. For example, the front and rear housing portions can be welded together (e.g., laser welded) along a weld zone 106 on each housing, to both seal and attach the housings. Alternatively, the front and rear housing portions can be adhered to each other, using an appropriate implantable grade epoxy bonding material for example. Mechanical fasteners can also be used to attach the housing portions, which can be sealed by a gasket for example.

A header 108 is mounted onto the housing portions 102, 104. The header 108 can be adhered to the housing portions 102, 104 using an appropriate implantable grade epoxy bonding material for example. The header 108 can be of molded elastomeric material, molded plastic, molded urethane, and the like, in particular if transparency of the header is desired. Alternatively, the header as a separate component could be avoided, and the entire housing could be comprised of the same material, such as that discussed for the front and rear housing portions 102, 104.

The header 108 can comprise one or more connectors. In the illustrated example, the header 108 includes two connectors 110, 112, which respectively correspond to bores 114, 116. Leads (not shown), such as cables, can be connected to the implantable medical device 100 via the header 108 and bores 114, 116. For example, the proximal ends of the leads can respectively be inserted into the bores 114, 116 to connect to the connectors 110, 112. That is, the proximal ends of leads can be plugged into the connectors comprised in the header 108 via the bores 114, 116. When plugged in (e.g., physically connected), the leads are electrically connected to control circuitry and a power supply contained within the housing portions 102, 104. The leads connect the implantable medical device to electrodes (not shown). The electrodes can be surgically secured to body tissue whose proper functioning is assisted by the implantable medical device 100, via pulsed electrical signals from the device for example (e.g., see FIG. 12 discussed hereinbelow). The electrodes can be used to control pain (e.g., back pain), treat epilepsy or paralasis, regulate cardiac activity, etc. Thus one end of each of the leads is electrically and physically connected to the implantable medical device 100 via the header 108, while the other end of each lead is placed in or near the tissue to be electrically stimulated (e.g., the spinal column). The second end of each lead includes or is connected to exposed electrodes. Thus, the exposed electrodes are electrically connected to the implantable medical device 100, and can transfer electrical stimulation pulses generated by the implantable medical device 100 to the tissue.

The connectors 110, 112 are enclosed with in the header 108 and connected to the leads, and thus the electrodes. The connectors 110, 112 each include a stack of contact blocks separated by seals. The contact blocks are connected to lead frames 118. The lead frames 118 extend from the contact blocks to feed through pins 120. The feed through pins (e.g., platinum pins) extend from the header 108 into the housing portions 102, 104 to connect to the circuitry therein.

Figure 2:
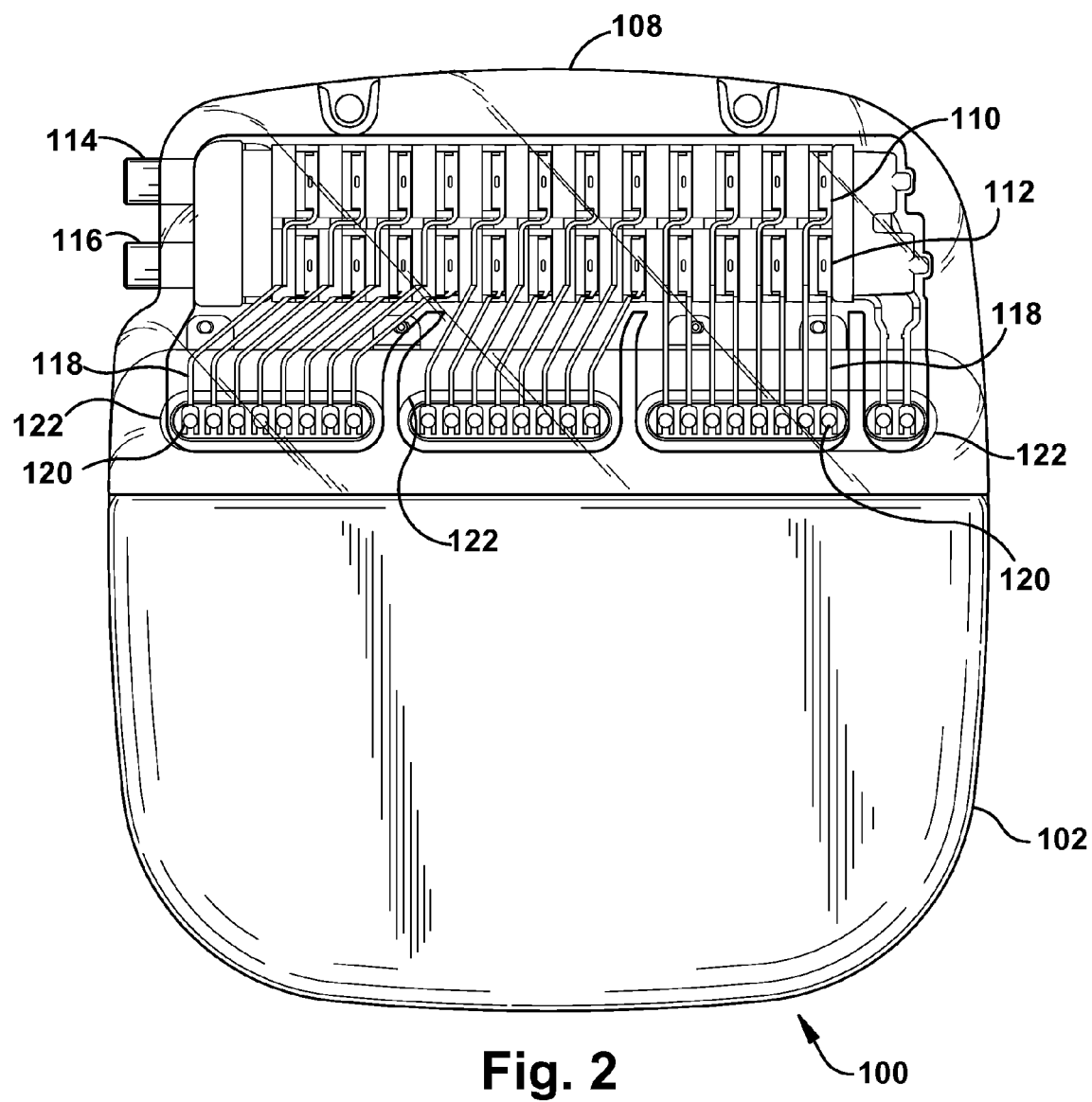
FIG. 2 is a front view of the implantable medical device of FIG. 1.

FIG. 2 is a front view of the implantable medical device shown in FIG. 1. It can be seen that the front housing portion 102 has a plurality of feed through holes 122, through which the lead frames 118 are connected to the feed through pins 120 for connecting to internal electronics of the implanted medical device. Thus, the feed through holes 122 provide access from the header to the interior space enclosed by the housing portions 102, 104. In the example embodiment illustrated in FIG. 2, the implantable medical device 100 includes three feed through holes 122.

Figure 3:
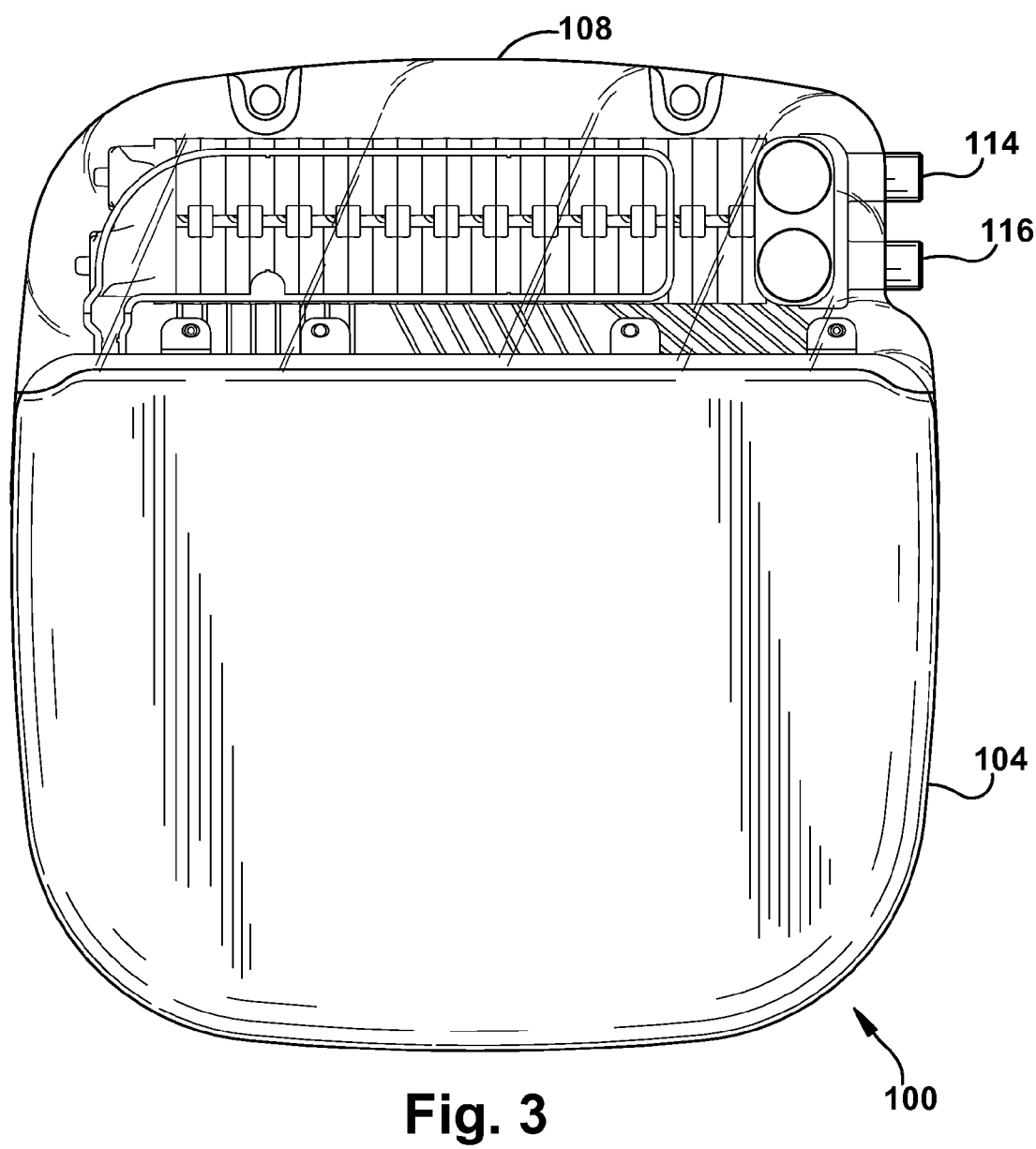
FIG. 3 is a rear view of the implantable medical device of FIG. 1.

FIG. 3 is a rear view of the implantable medical device shown in FIG. 1.

Figure 4:
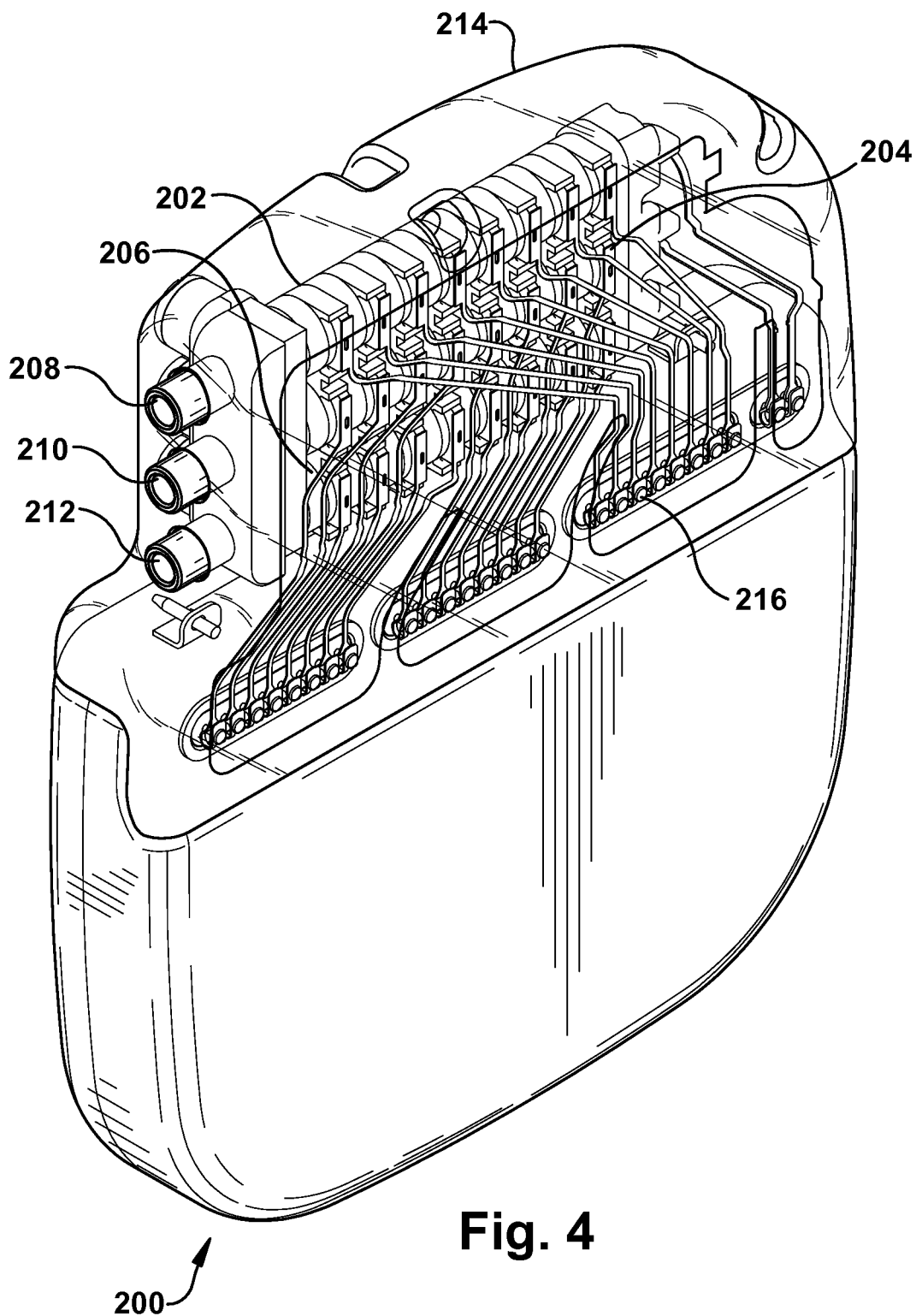
FIG. 4 is a perspective view of an example implantable medical device.

FIG. 4 is a perspective view of an example embodiment of another implantable medical device 200. The device 200 has three connectors 202, 204, 206 stacked vertically, instead of two as shown in FIG. 1. The device 200 also has three corresponding bores 208, 210, 212. The connectors 202, 204, 206 each have fewer contacts and thus are shorter than the connectors shown in FIG. 1. The header 214 is shaped differently than the header in FIG. 1, to accommodate the shorter but taller stacked group of connectors 202, 204, 206. The number of feed through pins 216 (e.g., 24 pins) is the same in both FIG. 4 and FIG. 1. It is to be appreciated that the embodiment shown in FIG. 4 can have fewer or a greater number of feed through pins than the embodiment shown in FIG. 1.

Figure 5:
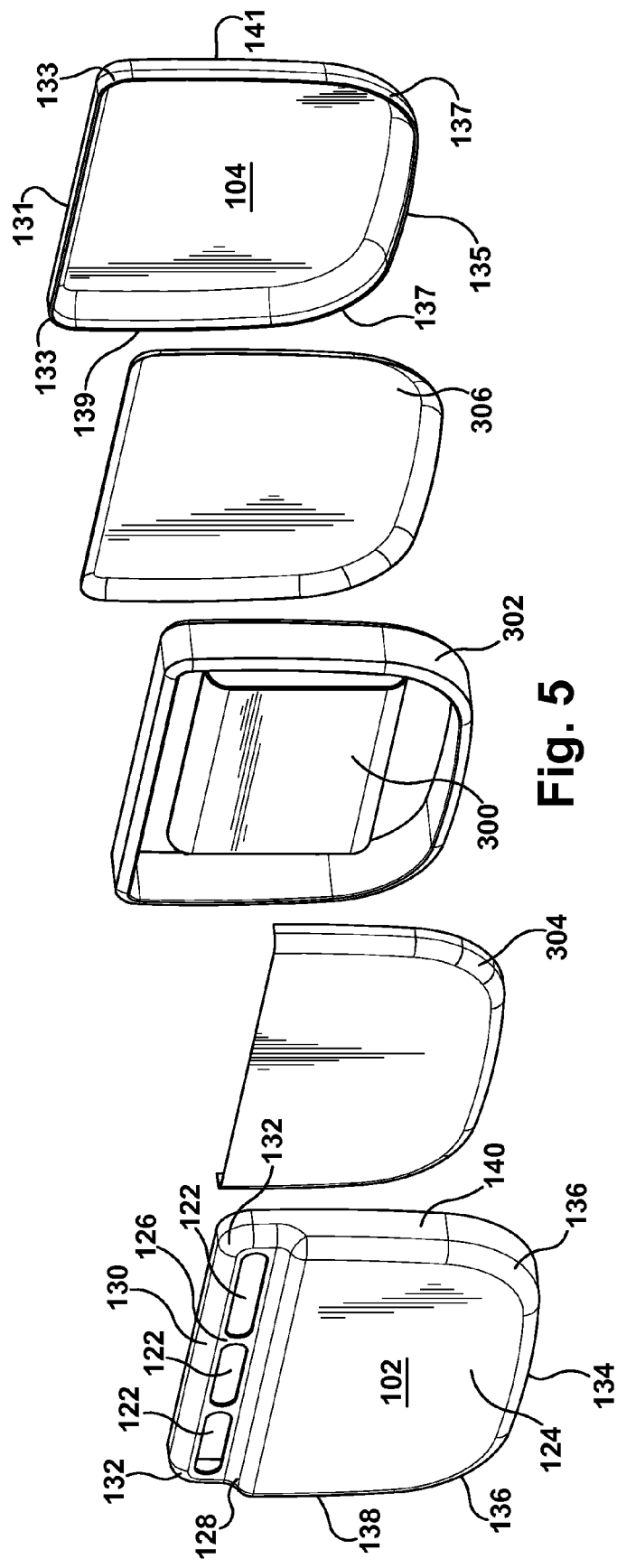
FIG. 5 is a partial exploded view of an example implantable medical device.

FIG. 5 is a partial exploded view of an implantable medical device. More specifically, FIG. 5 provides an exploded view of the housing portions and components housed within the housing portions. Pulse generation circuitry 300 including a battery and controller, which can include an application specific integrated circuit, are located within the housing portions 102, 104. A charging coil 302 is also located within the housing portions 102, 104. The charging coil 302 charges the battery via electromagnetic energy supplied by a non-contact charger located outside of the body. Heat spreader sheets 304, 306 draw heat from the coil 302 away from the peripheral portions of the housing portions 102, 104, toward more central portions of the housing, to help reduce the formation of hot spots along the housings. The heat spreader sheets 304, 306 can be formed from a graphite sheet material or other suitably conductive materials, and generally conform to the interior contours of the housing portions 102, 104. Examples of such heat spreader sheets are described in detail in co-pending application Ser. No. 13/359,739 incorporated herein by reference.

It can be seen in FIG. 5 that the front housing 102 includes a deep portion 124 and a shallow portion 126. A transition portion 128 joins the deep portion 124 and the shallow portion 126. The deep portion 124 is suitable for housing various parts of the pulse generation circuitry, such as the battery. The shallow portion 126 includes the feed through holes 122. The feed through pins 120 (FIGS. 1 and 2) are aligned with the feed through holes, as discussed above. The feed through holes 122 can be cut or punched into the shallow portion 126, after the front housing portion 102 is superplastically formed, as discussed below. The transition portion 128 can provide a shelf onto which the header 108 (FIGS. 1 and 2) is adhered and sealed.

Both the front housing portion 102 and the rear housing portion 104 have a first edge portion 130, 131. The first edge portions 130, 131 are shown as being substantially straight (e.g., extends along a substantially straight line). Alternatively, the first edge portions can be curved. The first edge portions 130, 131 extend between respective first sets of rounded corners 132, 133 on the front and rear housing portions 102, 104. The header 108 (FIGS. 1 and 2) can be adhered to one or both of the first edge portions 130, 131.

Both housing portions 102, 104 have a second edge portion 134, 135 that is located between a second set of rounded corners 136, 137. The second edge portion 134, 135 can be straight or rounded (e.g., extends along a curve between the second set of rounded corners). In FIG. 5, the second edge portion 134, 135 is rounded.

With respect to the front housing portion 102, it can be seen that the first edge portion 130 is located along the shallow portion 126, and the second edge portion 134 is located along the deep portion 124.

Both housing portions 102, 104 further have a third edge portion 138, 139 and a fourth edge portion 140, 141. The third edge portion 138, 139 extends between a rounded corner of the first set of rounded corners 132, 133 and a rounded corner of the second set of rounded corners 136, 137. Similarly, the fourth edge portion 140, 141 extends between the other rounded corner of the first set of rounded corners 132, 133 and the other rounded corner of the second set of rounded corners 136, 137. The third and fourth edge portions can be straight or curved. In FIG. 5, the third and fourth edge portions are curved.

The second, third and fourth edge portions can have different radii of curvature or the same radius of curvature. For example, the second through fourth edge portions can each have a radius of curvature of about 5.0 inches, providing these edge portions with a gently curved shape as shown.

The radius of curvature for the first set of rounded corners 132, 133 (i.e., the radii of each rounded corner) can be the same or different from the radius for the second set of rounded corners 136, 137. In an embodiment, the radius for the first set of rounded corners 132, 133 is substantially smaller than the radius for the second set of rounded corners 136, 137. For example, the radius for the second set of rounded corners 136, 137 can be about twice the radius of the first set of rounded corners 132, 133, between two and three times the radius of the first set of rounded corners, between three and four times the radius of the first set of rounded corners, greater than four times the radius of the first set of rounded corners, etc. In an example embodiment, the radius for the first set of rounded corners 132, 133 is nominally 0.137 inches, and the radius for the second set of rounded corners 136, 137 is nominally 0.500 inches.

It is to be appreciated that the radius for the first set of rounded corners 132, 133 is small, making the titanium alloy housing portions 102, 104 better suited for superplastic forming than conventional cold and hot stamping. The housing portions 102, 104 have further tight curves of small radii that make the housing portions better suited for thermoplastic forming. For example, each housing portion 102, 104 is cupped upward toward the welding zone 106 (FIG. 1) to form an inner cavity for housing the pulse generation circuitry and coil. The radii for the upward bends in the housing portions 102, 104 that form the cupped shaped and interior cavities can be smaller than the radius for the first set of rounded corners. Example radii for the upward bends in the housing portions 102, 104 are between 0.072 and 0.100 inches. The front housing portion 102 has additional tight curves at the junction between the deep portion 124 and the transition portion 128 and the junction between the shallow portion 126 and the transition portion 128. Example radii for the curves at the transition portion 128 are between 0.072 and 0.066 inches.

It is to be appreciated that the radii discussed herein are examples, and that radii of various sizes can be used in the housing portions 102, 104. Further, curves discussed collectively with reference to a common radius can have radii of different sizes.

Figure 6:
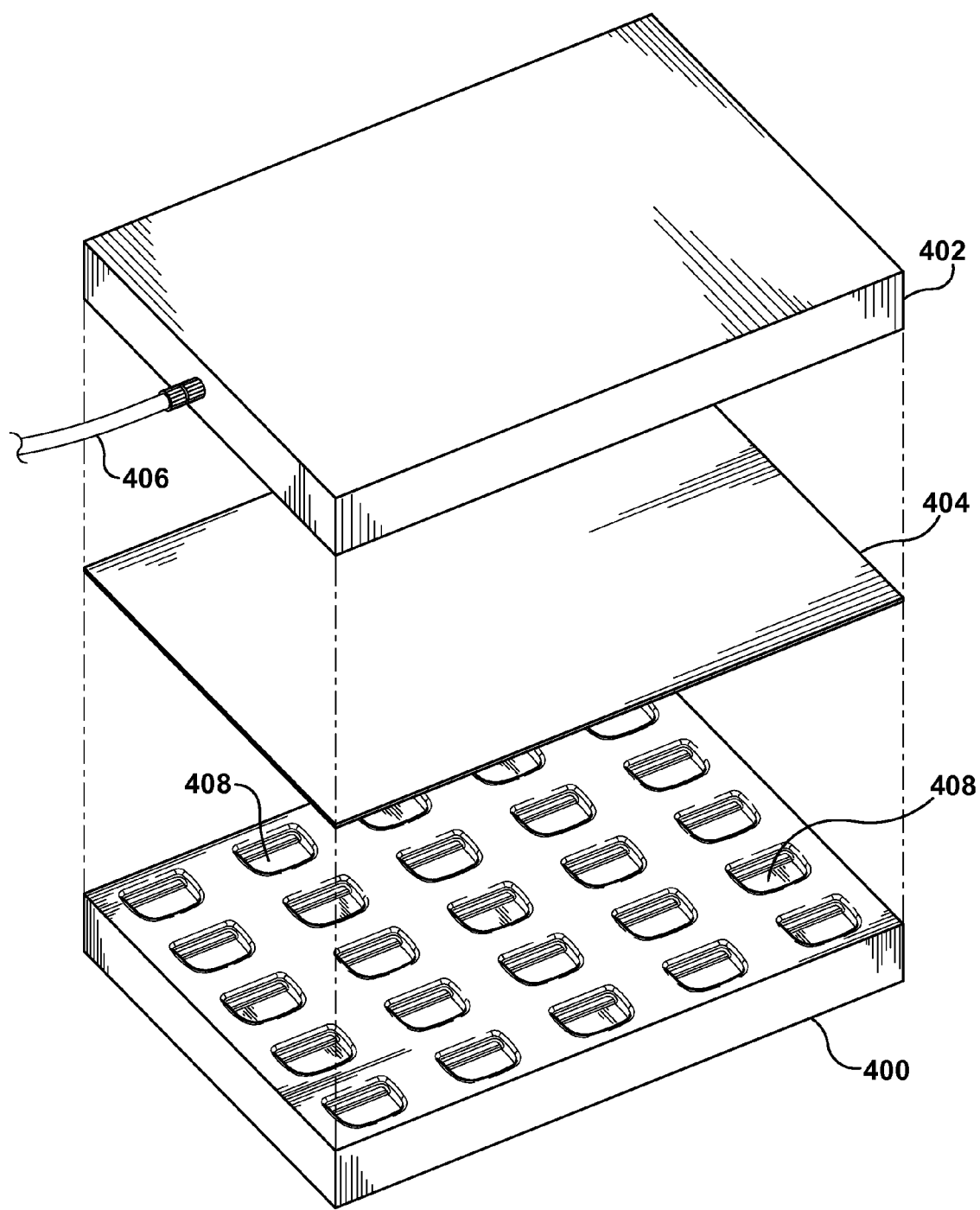
FIG. 6 is a schematic diagram of a system for superplastically forming a workpiece comprising a plurality of housing portions for implantable medical devices.

FIG. 6 is a schematic diagram of a system for superplastic forming the titanium alloy housing portions 102, 104. The system includes a die 400 and a press 402. A titanium alloy metal sheet 404 is placed between the die 400 and the press 402 and heated to a suitable superplastic forming temperature. The metal sheet 404 can be heated by one or both of the die 400 and the press 402, or the metal sheet 404 can be heated by heaters external to the die and press.

The press 402 forces the heated titanium alloy metal sheet 404 onto the die 400, to superplastically form a work piece comprising a plurality of integrally formed and joined housing portions. The press 402 can use the pressure of a gas, such as an inert gas (e.g., argon), to slowly force the heated metal sheet 404 against the die 400. In FIG. 6, gas is supplied to the press 402 via a hose 406.

The die 400 has a plurality of housing forming areas 408 that each correspond to one housing portion to be superplastically formed. The housing forming areas 408 can be arranged in a matrix as shown. The housing forming areas 408 can be profiled to form identical housing portions, such as the front housing portion 102 (FIG. 1) or different housing portions, such as both the front and rear housing portions 102, 104. The die 400 can have any number of housing forming areas 408, to form a workpiece having a corresponding number of integrally formed and joined housing portions. For example, the die can have eight housing forming areas 408 (e.g., arranged in a 4×2 matrix) to form a workpiece with eight joined housings, the die can have sixteen housing forming areas (e.g., arranged in a 4×4 matrix) to form a workpiece with sixteen joined housings, the die can have twenty-five housing forming areas (e.g., arranged in a 5×5 matrix) to form a workpiece with twenty-five joined housings, etc.

Figure 7:
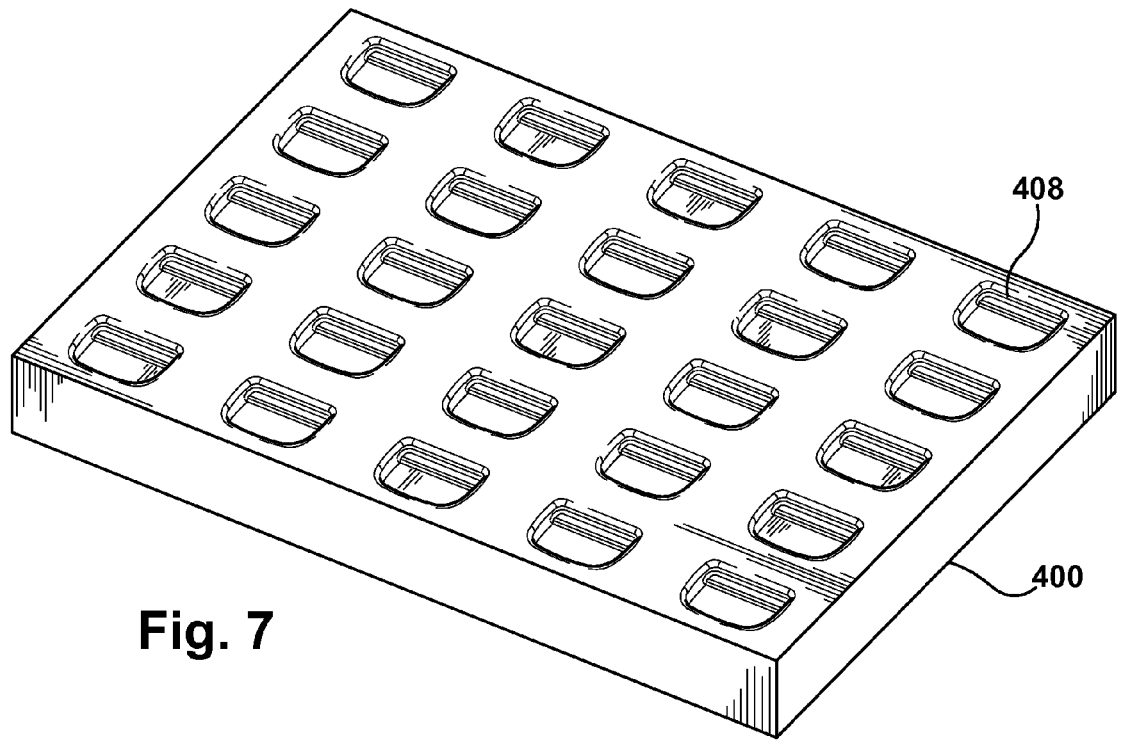
FIG. 7 is a perspective view of an example die.
Figure 8:
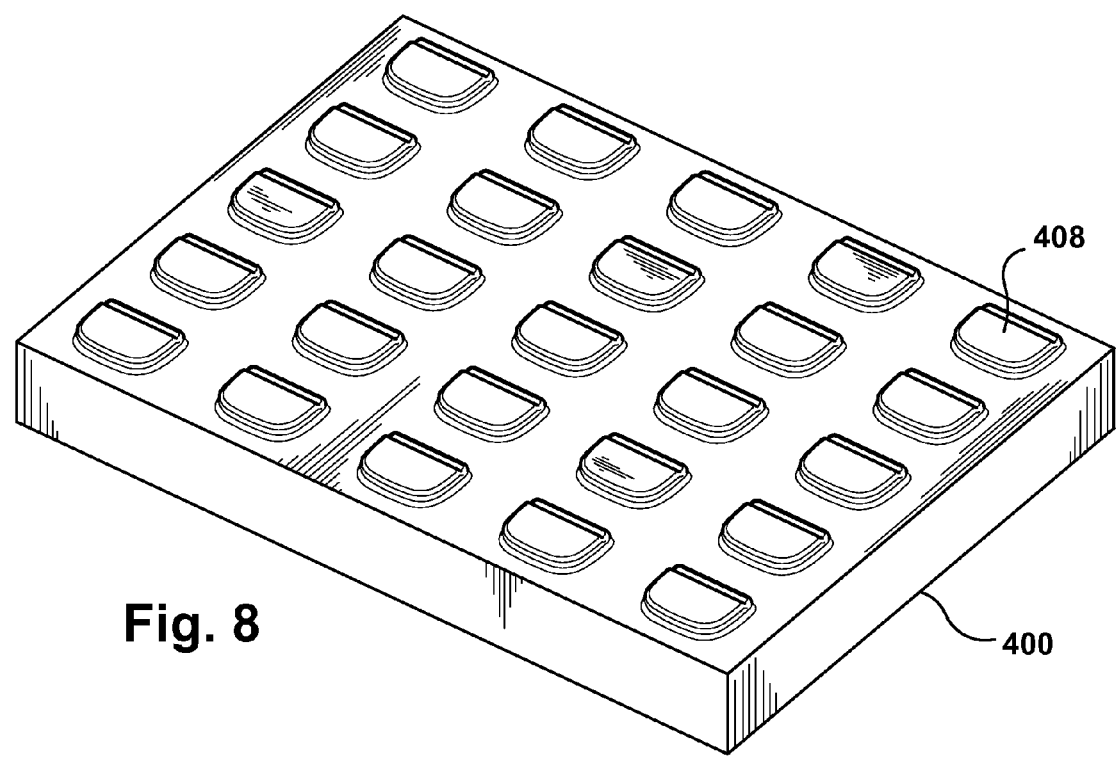
FIG. 8 is a perspective view of an example die.

The press 402 forces the heated titanium alloy metal sheet 404 over each of the forming areas 408 generally simultaneously, thereby simultaneously forming the plurality of housing portions in the workpiece. The forming areas 408 of the die 400 can be either cavities or projections. With cavities, respective portions of the metal sheet 404 are pressed into each one of the cavities to mold the housing portions within the cavities. With projections, as the metal sheet 404 is pressed onto the die 400, the projections press into the sheet, and the contours of the projections form the housing portions. An example die 400 with twenty-five cavities as forming areas 408 is shown in FIG. 7. An example die 400 with twenty-five projections as forming areas 408 is shown in FIG. 8.

Figure 9:
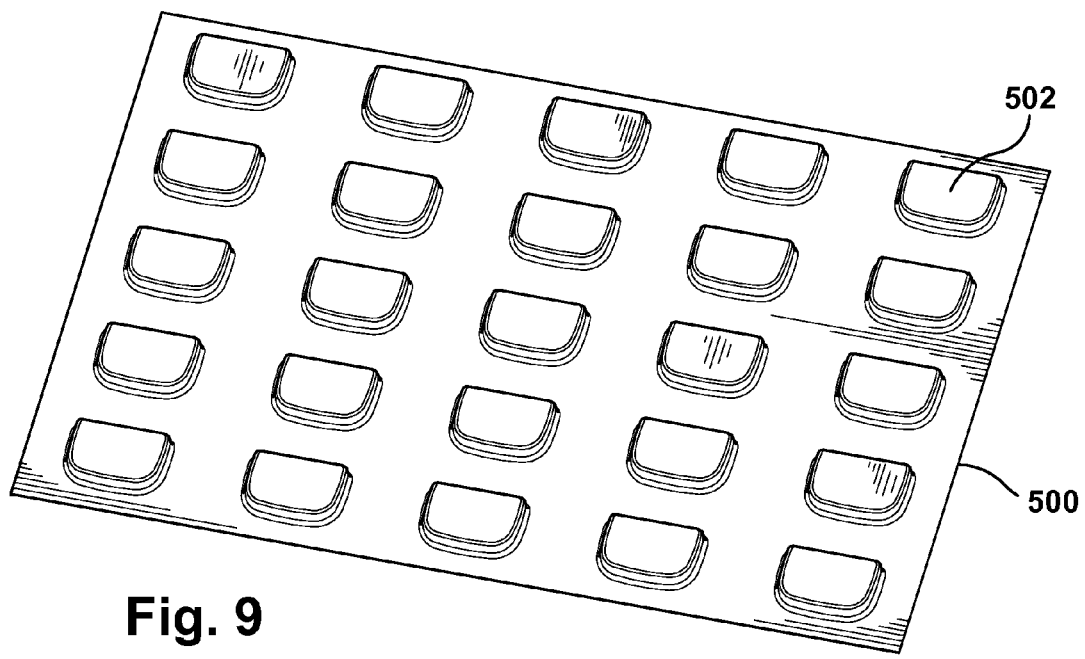
FIG. 9 is a perspective view of an example workpiece.
Figure 10:
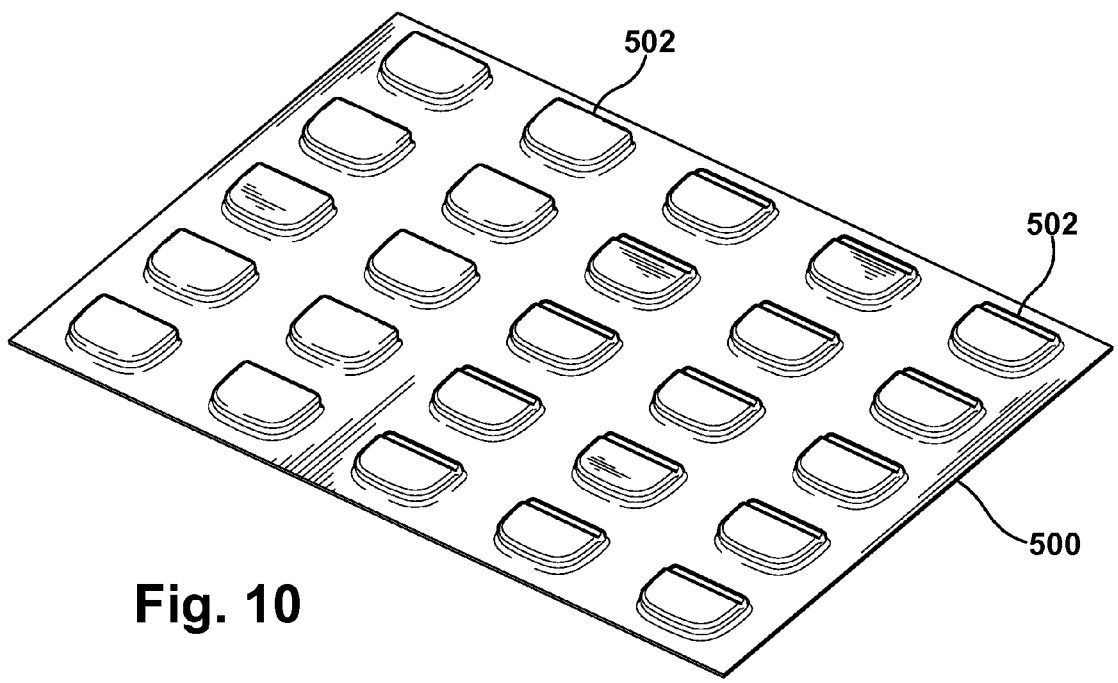
FIG. 10 is a perspective view of an example workpiece.

FIG. 9 shows an example workpiece 500 superplastically formed by the press 402 and die 400 (FIG. 6) and having a plurality of joined and integrally formed housing portions 502. It can be seen that the workpiece 500 has an appearance similar to a muffin pan. In FIG. 9, each of the joined housing portions 502 has the same shape, e.g., the shape of the rear housing portion. However, FIG. 10 shows a workpiece having housings 502 for both the front housing portion 102 and the rear housing portion 104 (FIG. 1). Thus, multiple implantable medical devices can be constructed from the single workpiece 500 shown in FIG. 10.

After the workpiece 500 is formed, for example after the workpiece cools, the plurality of joined housing portions 502 can be separated (e.g., cut or punched) into separate housing portions. The separated housing portions can undergo a final trimming by cutting, grinding, or otherwise machining them. The housing portions can also be acid etched, for example to clean them. Acid etching can occur before and/or after housing portions are separated. The housing portions can undergo additional metalworking processes such as polishing, shot peening, bead blasting, etc. For front housing portions 102 (FIG. 2), the feed through holes 122 will be cut or punched from the shallow portion 126 (FIG. 5).

Figure 11:
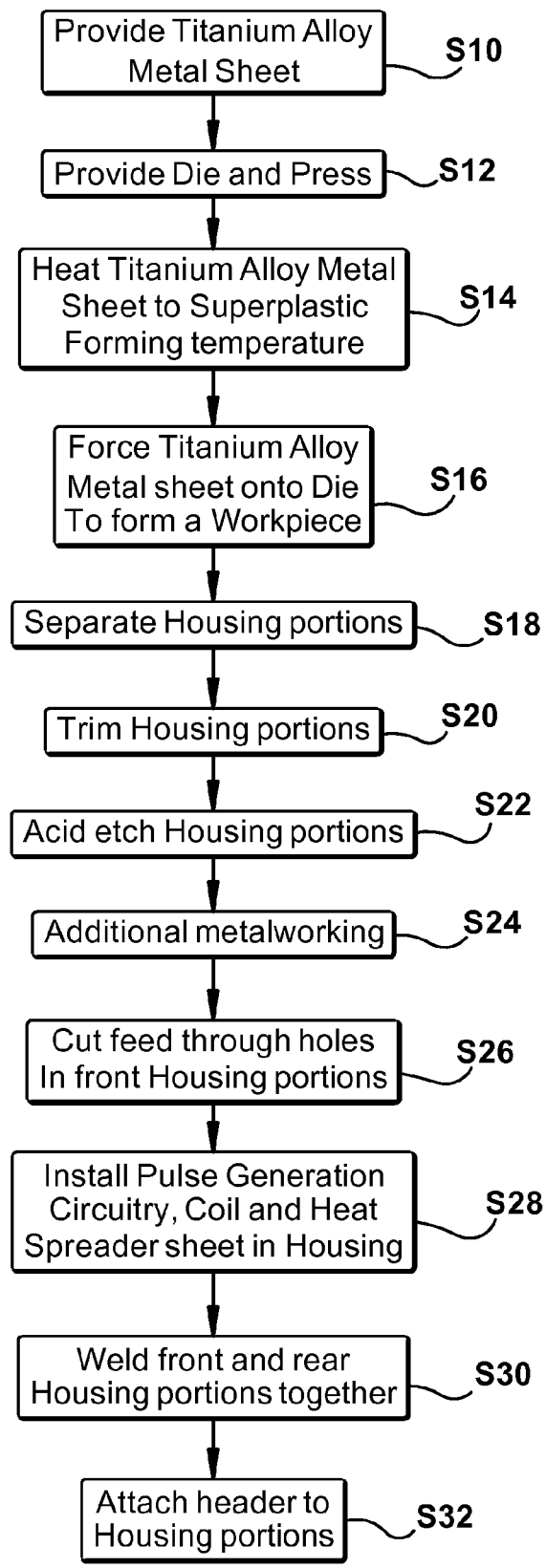
FIG. 11 is a flow diagram.

FIG. 11 is a flow diagram of example processing steps for forming the housing portions and the implantable medical device. Initially, the titanium alloy metal sheet (S10) and the die and press (S12) are provided. The die has a plurality of housing forming areas (e.g., cavities or projections) as described above. The titanium alloy metal sheet is heated to a superplastic forming temperature (S14) and forced onto the die to form the workpiece (S16). The housing portions are separated from the workpiece (S18), trimmed (S20) and acid etched (S22). Additional metalworking (S24) can be performed on the housing portions, such as polishing, shot peening, bead blasting, etc. Feed through holes are cut into the front housing portions (S26). Pulse generation circuitry, charging coils, and heat spreader sheets are installed in the housing portions (S28). Front and rear housing portions are welded together (S30), and the header is attached to the housing portions (S32).

Figure 12:
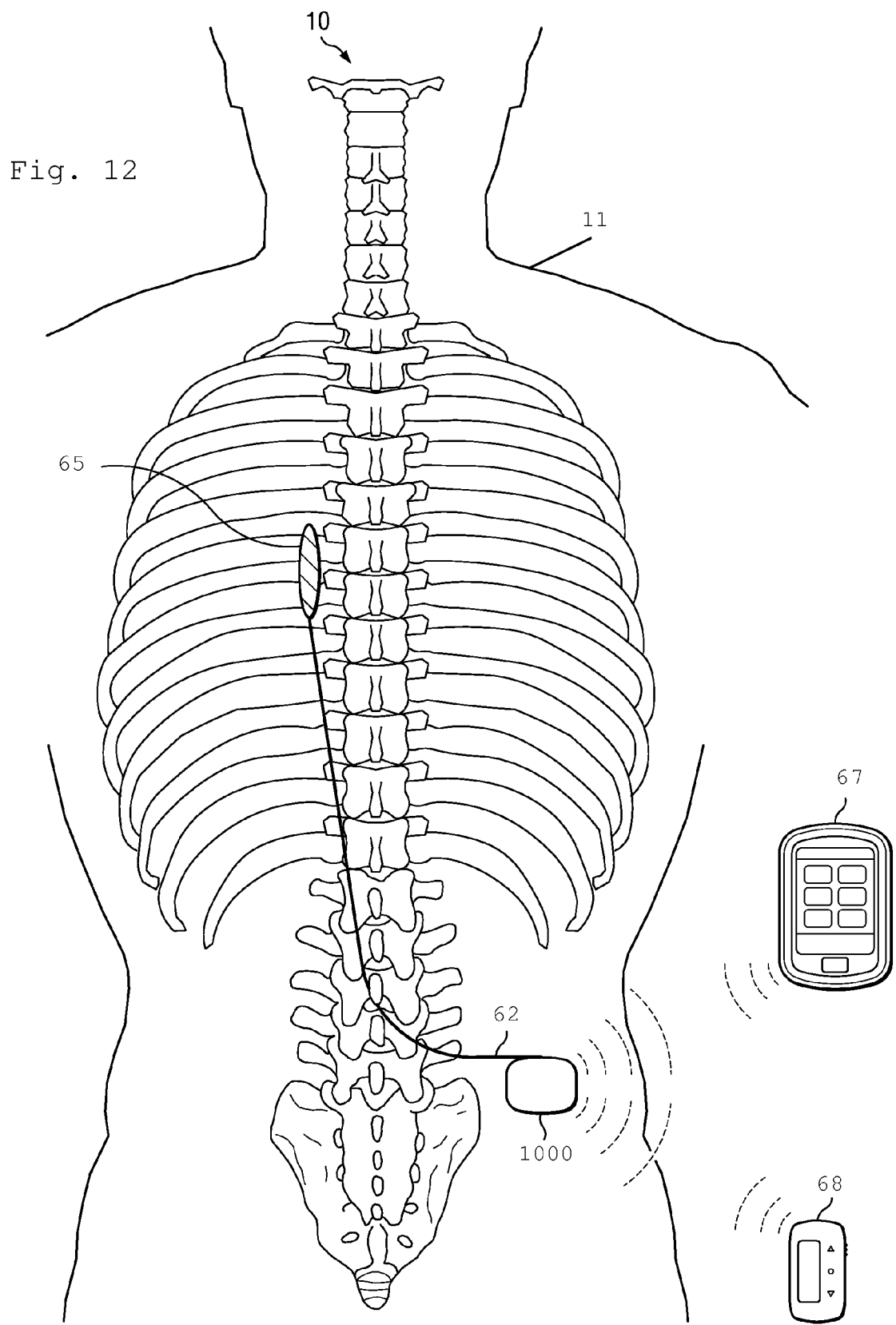
FIG. 12 is a schematic of an example implanted medical device.

FIG. 12 shows an example application of an implanted medical device for providing spinal stimulation to a patient 11. In that figure, the implanted medical device is an implantable pulse generator (IPG) 1000 shown implanted in a patient 900 for providing pulse stimulation of the patient's spinal cord (in the spine 10) for the purpose of providing pain therapy. The IPG 1000 can be comprised of an internal power supply (that may include a rechargeable battery), a controller, pulse generation electronics, protection/conditioning circuits, and a contact assembly for connecting to an electrode array. The IPG 1000 can be supported by an external power supply (such as for charging the battery of the internal power supply), and a clinician programmer 67 and a user controller 68. Also shown is the human spine 10 in proximity with the stimulation electrodes 65 that are attached to the IPG 1000 via electrode leads 62.

The leads and electrodes may be positioned anywhere along the spine to deliver the intended therapeutic effects of spinal cord electrical stimulation in the desired region of the spine. The distal end of the lead with its accompanying electrodes may be located along the epidural space and adjacent a desired portion of the spinal cord using well-established and known techniques for implanting and positioning SCS leads and electrodes, and the IPG 1000 may be programmed using a clinician programmer 67 or other type of programmer 68 (such as a patient controller), as desired. The electrode leads 62 can be connected to the IPG via a contact assembly as described in this application.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. A method of manufacturing a plurality of titanium alloy implantable medical device housing portions, comprising the steps of:
   a) providing a titanium alloy metal sheet;
   b) heating the titanium alloy metal sheet to a superplastic forming temperature;
   c) providing a die comprising a plurality of housing forming areas each corresponding to one of said housing portions; and
   d) forcing the heated titanium alloy metal sheet onto the die for engaging each one of the plurality of housing forming areas, thereby superplastically forming a workpiece comprising a plurality of integrally formed implantable medical device housing portions.

2. The method of claim 1, wherein the titanium alloy is selected from the group consisting of Ti-6Al-4V ELI alloy and Ti-3Al-2.5V alloy.

3. The method of claim 1, wherein the plurality of integrally formed implantable medical device housing portions includes a plurality of front housing portions, and a plurality of rear housing portions that are different from the front housing portions.

4. The method of claim 1, wherein the workpiece comprises at least twenty-five integrally formed implantable medical device housing portions.

5. The method of claim 1, wherein the plurality of housing forming areas comprises a plurality of contoured projections from a surface of the die.

6. The method of claim 1, wherein the plurality of housing forming areas comprises a plurality of cavities into which respective portions of the heated titanium alloy metal sheet are forced.

7. The method of claim 1, further comprising the steps of:
   a) separating the plurality of integrally formed implantable medical device housing portions into separate housing portions;
   b) trimming the plurality of separate housing portions; and
   c) acid etching the plurality of implantable medical device housing portions before and/or after performing the step of separating.

8. The method of claim 1, wherein each housing portion includes a first edge portion located between a first set of rounded corners, and a second edge portion located between a second set of rounded corners, and wherein a radius for the second set of rounded corners is at least three times larger than a radius for the first set of rounded corners,
   wherein the first edge portion extends along a substantially straight line between the first set of rounded corners, and the second edge portion extends along a curve between the second set of rounded corners,
   wherein each housing portion includes third and fourth edge portions extending between the first set of rounded corners and the second set of rounded corners, and wherein the third and fourth edge portions are curved.

9. The method of claim 8, wherein each housing portion includes a deep portion having a first depth, a shallow portion having a second depth, and a transition portion joining the deep portion and the shallow portion, and wherein the first edge portion is located along the shallow portion and the second edge portion is located along the deep portion, the method further comprising the step of cutting a plurality of feed through holes into the shallow portion of each housing portion.

10. A method of manufacturing a plurality of titanium alloy implantable medical device housing portions, comprising the steps of:
    providing a titanium alloy metal sheet;
    heating the titanium alloy metal sheet to a superplastic forming temperature
    providing a die comprising a plurality of housing forming areas each corresponding to one of said housing portions, said housing forming areas arranged in a plurality of rows and a plurality of columns; and
    forcing the heated titanium alloy metal sheet onto the die for engaging each one of the plurality of housing forming areas, thereby superplastically forming a workpiece comprising a plurality of integrally formed implantable medical device housing portions arranged in said plurality of rows and plurality of columns corresponding to said forming areas of said die.

11. The method of claim 10, further comprising the step of separating the plurality of integrally formed implantable medical device housing portions into individual units.

12. The method of claim 10, further comprising the step of separating the plurality of integrally formed implantable medical device housing portions into individual units, said method further including the steps of:
    further working at least some of said units to form a plurality of first units;
    further working at least some others of said units to form a plurality of second units; and
    assembling a plurality of implantable medical devices by, for each one of said implantable medical device, sealing electronics in an inner chamber formed by connecting one of the first units to one of the second units.

13. A method of manufacturing a plurality of titanium alloy implantable medical device housing portions, comprising the steps of:
    providing a titanium alloy metal sheet;
    heating the titanium alloy metal sheet to a superplastic forming temperature;
    providing a die comprising a plurality of housing forming areas each corresponding to one of said housing portions, said housing forming areas arranged in a plurality of rows and a plurality of columns;
    forcing the heated titanium alloy metal sheet onto the die for engaging each one of the plurality of housing forming areas, thereby superplastically forming a workpiece comprising a plurality of integrally formed implantable medical device housing portions arranged in said plurality of rows and plurality of columns corresponding to said forming areas of said die, wherein at least some of said housing portions are used to provide a plurality of first units;
    providing a plurality of second units; and
    assembling a plurality of implantable medical devices by, for each one of said implantable medical device, sealing electronics in an inner chamber formed by connecting one of the first units to one of the second units.

14. The method of claim 13, wherein said plurality of second units are worked differently than said plurality of first units.

* * * * *